(12) United States Patent
Locke et al.

(10) Patent No.: US 9,345,821 B2
(45) Date of Patent: May 24, 2016

(54) REDUCED-PRESSURE SOURCES, SYSTEMS, AND METHODS EMPLOYING A POLYMERIC, POROUS, HYDROPHOBIC MATERIAL

(71) Applicant: KCI Licensing, Inc., San Antonio, TX (US)

(72) Inventors: Christopher Brian Locke, Bournemouth (GB); Timothy Mark Robinson, Basingstoke (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 31 days.

(21) Appl. No.: 14/218,582

(22) Filed: Mar. 18, 2014

(65) Prior Publication Data

US 2014/0200534 A1   Jul. 17, 2014

Related U.S. Application Data

(63) Continuation of application No. 13/084,742, filed on Apr. 12, 2011, now Pat. No. 8,702,665.

(60) Provisional application No. 61/359,205, filed on Jun. 28, 2010, provisional application No. 61/359,181, filed on Jun. 28, 2010, provisional application No. 61/325,115, filed on Apr. 16, 2010.

(51) Int. Cl.
*A61M 1/00* (2006.01)
*A61F 13/02* (2006.01)
*A61F 13/00* (2006.01)

(52) U.S. Cl.
CPC .............. *A61M 1/0023* (2013.01); *A61F 13/02* (2013.01); *A61F 13/0223* (2013.01);

(Continued)

(58) Field of Classification Search
USPC .............................................. 604/8
See application file for complete search history.

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Tatyana Zalukaeva
*Assistant Examiner* — Guy K Townsend

(57) ABSTRACT

Reduced-pressure sources, systems, and methods involve using a vacuum pump that is disposed within a sealed space to produce reduced pressure. The exhaust from the vacuum pump is exhausted from the sealed space through pores in an enclosure member that is made of a polymeric, porous, hydrophobic material. Other devices, systems, and methods are disclosed.

20 Claims, 4 Drawing Sheets

(52) U.S. Cl.
CPC ............ *A61M 1/0001* (2013.01); *A61M 1/009* (2014.02); *A61M 1/0031* (2013.01); *A61M 1/0052* (2014.02); *A61M 1/0088* (2013.01); *A61F 2013/0074* (2013.01); *A61F 2013/00536* (2013.01); *A61M 1/0058* (2013.01); *A61M 1/0066* (2013.01); *A61M 2205/7527* (2013.01); *A61M 2205/7536* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,565,635 A * | 1/1986 | Le Du | C02F 1/52 210/727 |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,061,258 A * | 10/1991 | Martz | A61F 13/023 128/898 |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,591,790 A * | 1/1997 | Lock | D04H 1/42 156/283 |
| 5,593,395 A * | 1/1997 | Martz | A61F 13/023 602/58 |
| 5,607,388 A | 3/1997 | Ewall | |
| 5,636,643 A | 6/1997 | Argenta et al. | |
| 5,645,081 A | 7/1997 | Argenta et al. | |
| 5,986,163 A * | 11/1999 | Augustine | A61F 7/007 602/2 |
| 6,071,254 A * | 6/2000 | Augustine | A61F 7/007 602/2 |
| 6,071,267 A | 6/2000 | Zamierowski | |
| 6,135,116 A | 10/2000 | Vogel et al. | |
| 6,213,966 B1 * | 4/2001 | Augustine | A61F 7/007 602/2 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,419,651 B1 * | 7/2002 | Augustine | A61F 7/007 602/2 |
| 6,420,622 B1 * | 7/2002 | Johnston | A47L 9/02 428/167 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,566,575 B1 * | 5/2003 | Stickels | A61F 13/023 602/41 |
| 6,814,079 B2 | 11/2004 | Heaton et al. | |
| 6,840,915 B2 * | 1/2005 | Augustine | A61F 7/007 602/2 |
| 7,108,683 B2 * | 9/2006 | Zamierowski | A61M 1/0058 604/304 |
| 7,198,046 B1 * | 4/2007 | Argenta | A61M 1/005 128/897 |
| 7,216,651 B2 * | 5/2007 | Argenta | A61M 1/005 128/897 |
| 7,438,705 B2 * | 10/2008 | Karpowicz | A61M 1/0001 604/313 |
| 7,477,939 B2 * | 1/2009 | Sun | A61N 1/30 604/20 |
| 7,615,036 B2 * | 11/2009 | Joshi | A61M 1/0088 602/42 |
| 7,772,455 B1 * | 8/2010 | Roe | A61F 13/42 604/360 |
| 7,909,805 B2 * | 3/2011 | Weston | A61M 1/0001 604/313 |
| 8,062,272 B2 * | 11/2011 | Weston | A61M 1/0031 128/888 |
| 8,177,763 B2 * | 5/2012 | Wiesner | A61M 1/0049 604/313 |
| 2002/0077661 A1 | 6/2002 | Saadat | |
| 2002/0115951 A1 | 8/2002 | Norstrem et al. | |
| 2002/0120185 A1 | 8/2002 | Johnson | |

(56) References Cited

U.S. PATENT DOCUMENTS

| | | | |
|---|---|---|---|
| 2002/0128578 A1* | 9/2002 | Johnston | A47L 9/02 602/43 |
| 2002/0143286 A1 | 10/2002 | Tumey | |
| 2002/0183676 A1* | 12/2002 | Augustine | A61F 7/007 602/42 |
| 2003/0040687 A1* | 2/2003 | Boynton | A61M 1/0031 601/6 |
| 2003/0050594 A1* | 3/2003 | Zamierowski | A61M 1/0058 604/46 |
| 2003/0144619 A1* | 7/2003 | Augustine | A61F 7/007 602/2 |
| 2004/0006319 A1* | 1/2004 | Lina | A61F 13/0203 604/304 |
| 2005/0077225 A1* | 4/2005 | Usher | A61M 5/1408 210/321.6 |
| 2005/0222544 A1* | 10/2005 | Weston | A61M 1/0001 604/313 |
| 2005/0261642 A1* | 11/2005 | Weston | A61M 1/0031 604/313 |
| 2006/0020235 A1* | 1/2006 | Siniaguine | A61F 13/00995 602/41 |
| 2006/0079852 A1 | 4/2006 | Bubb et al. | |
| 2007/0016152 A1* | 1/2007 | Karpowicz | A61M 1/0001 604/326 |
| 2007/0038172 A1* | 2/2007 | Zamierowski | A61M 1/0088 604/20 |
| 2007/0129707 A1* | 6/2007 | Blott | A61M 1/0058 604/543 |
| 2007/0141128 A1* | 6/2007 | Blott | A61M 1/0058 424/445 |
| 2007/0167926 A1* | 7/2007 | Blott | A61M 1/0084 604/304 |
| 2007/0219513 A1* | 9/2007 | Lina | A61F 13/0203 604/304 |
| 2007/0219532 A1* | 9/2007 | Karpowicz | A61M 1/0031 604/540 |
| 2007/0265585 A1* | 11/2007 | Joshi | A61M 1/0088 604/313 |
| 2007/0265586 A1* | 11/2007 | Joshi | A61M 1/0031 604/313 |
| 2008/0020127 A1* | 1/2008 | Whiteford | A01N 43/90 427/2.1 |
| 2008/0082059 A1* | 4/2008 | Fink | A61M 1/0001 604/305 |
| 2008/0167594 A1* | 7/2008 | Siniaguine | A61F 13/00021 602/48 |
| 2008/0171726 A1* | 7/2008 | Roth | A01N 1/02 514/144 |
| 2009/0221990 A1* | 9/2009 | Jaeb | A61M 1/0001 604/540 |
| 2011/0054423 A1* | 3/2011 | Blott | A61M 1/0058 604/319 |

FOREIGN PATENT DOCUMENTS

| | | |
|---|---|---|
| AU | 755496 | 2/2002 |
| CA | 2005436 | 6/1990 |
| CN | 101227937 A | 7/2008 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2009066105 A1 | 5/2009 |
| WO | 2009111655 A2 | 9/2009 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

(56) References Cited

OTHER PUBLICATIONS

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

REDUCED-PRESSURE SOURCES, SYSTEMS, AND METHODS EMPLOYING A POLYMERIC, POROUS, HYDROPHOBIC MATERIAL

RELATED APPLICATIONS

This application is a continuation of U.S. Non-Provisional patent application Ser. No. 13/084,742, entitled "Reduced Pressure Resources, Systems and Methods Employing A Polymeric, Porous, Hydrophobic Material," filed Apr. 12, 2011, which claims the benefit, under 35 USC §119(e), of: U.S. Provisional Patent Application Ser. No. 61/359,205, entitled "Evaporative Body Fluid Containers and Methods," filed Jun. 28, 2010; U.S. Provisional Patent Application Ser. No. 61/359,181, entitled "Dressings and Methods For Treating a Tissue Site On A Patient," filed Jun. 28, 2010; and U.S. Provisional Patent Application Ser. No. 61/325,115, entitled "Reduced-Pressure Sources, Systems, and Methods Employing A Polymeric, Porous, Hydrophobic Material," filed Apr. 16, 2010, which are incorporated herein by reference for all purposes.

BACKGROUND

The present disclosure relates generally to reduced-pressure medical treatment systems and, more particularly, but not by way of limitation, to reduced-pressure sources, systems, and methods.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad distributes reduced pressure to the tissue and channels fluids that are drawn from the tissue.

SUMMARY

According to an illustrative embodiment, a reduced-pressure source for use with a reduced-pressure system for treating a tissue site on a patient includes an enclosure member forming, at least in part, a sealed space and a vacuum pump disposed within the sealed space. The reduced-pressure source also includes a reduced-pressure outlet fluidly coupled to the vacuum pump for delivering reduced pressure and includes an exhaust outlet fluidly coupled to the vacuum pump for delivering an exhaust gas from the vacuum pump to the sealed space. The enclosure member comprises a polymeric, porous, hydrophobic material for allowing the exhaust gas to exit the sealed space.

According to another illustrative embodiment, a system for treating a tissue site on a patient with reduced pressure includes a treatment manifold for placing proximate to the tissue site for distributing reduced pressure to the tissue site, a reduced-pressure source fluidly coupled to the treatment manifold for providing reduced pressure to the treatment manifold, and a sealing member for forming a fluid seal over the tissue site. The reduced-pressure source includes an enclosure member forming, at least in part, a sealed space, and includes a vacuum pump disposed in the sealed space. The reduced-pressure source also includes a reduced-pressure outlet fluidly coupled to the vacuum pump for delivering reduced pressure and an exhaust outlet fluidly coupled to the vacuum pump for delivering an exhaust gas from the vacuum pump to the sealed space. The enclosure member comprises a polymeric, porous, hydrophobic material for allowing the exhaust gas to exit the sealed space.

According to another illustrative embodiment, a method of generating reduced pressure for use with a reduced-pressure system for treating a tissue site on a patient includes forming a sealed space and disposing a vacuum pump within the sealed space. At least a portion of the sealed space is formed by an enclosure member comprising a polymeric, porous, hydrophobic material. The vacuum pump includes a reduced-pressure outlet and an exhaust outlet. The enclosure member allows the exhaust gas to exit the sealed space. The method further includes exhausting the exhaust gas substantially from the sealed space through the enclosure member and delivering the reduced pressure to a desired location.

According to another illustrative embodiment, a method of manufacturing a reduced-pressure source for use with a reduced-pressure system for treating a tissue site on a patient includes forming an enclosure member for enclosing, at least in part, a sealed space and disposing a vacuum pump within the sealed space. The vacuum pump includes a reduced-pressure outlet fluidly coupled to the vacuum pump for delivering reduced pressure and an exhaust outlet fluidly coupled to the vacuum pump for delivering an exhaust gas from the vacuum pump to the sealed space. The step of forming an enclosure member includes forming an enclosure member from a polymeric, porous, hydrophobic material that allows the exhaust gas to exit the sealed space.

According to another illustrative embodiment, a dressing for treating a tissue site on a patient with reduced pressure includes a treatment manifold for placing proximate to the tissue site, an absorbent layer for receiving and retaining fluids from the tissue site, and a micro-pump having an exhaust outlet. The micro-pump generates reduced pressure and an exhaust that exits the exhaust outlet. The dressing further includes an enclosing cover for covering treatment manifold, the absorbent layer, and the micro-pump. The enclosing cover forms a sealed space. At least a portion of the enclosing cover is formed from a polymeric, porous, hydrophobic material that allows the exhaust to egress the sealed space.

According to another illustrative embodiment, a method for treating a tissue site on a patient includes disposing a treatment manifold proximate to the tissue site, disposing an absorbent layer over the treatment manifold for receiving fluids from the tissue site, and fluidly coupling a micro-pump to the absorbent layer. The method further includes covering the treatment manifold, absorbent layer, and micro-pump with an enclosing cover to form a sealed space. The sealed space has a first portion and a second portion. The micro-pump includes an exhaust outlet and a reduced-pressure outlet. The first portion of the sealed space is fluidly coupled to the micro-pump and receives exhaust from the exhaust outlet. The second portion of the sealed space is fluidly coupled to the micro-pump and receives reduced pressure. At least a portion of the enclosing cover is formed from a polymeric, porous, hydrophobic material that allows the exhaust to egress the first portion of the sealed space. The method also includes activating the micro-pump to produce reduced pressure and an exhaust and allowing the exhaust from the micro-pump to exit the sealed space through the enclosing cover.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

According to an illustrative embodiment, a reduced-pressure source 140, 240, 340, 440 is provided that is substantially liquid-tight such that liquids on an exterior of the reduced-pressure source 140, 240, 340, 440 cannot enter the reduced-pressure source 140, 240, 340, 440, but gases or vapors can exit the reduced-pressure source 140, 240, 340, 440. In this way, a user may engage in activities involving liquids, e.g., a shower or sweat-producing exercise, without the potential for liquids to enter the reduced-pressure source 140, 240, 340, 440.

Figure 1:
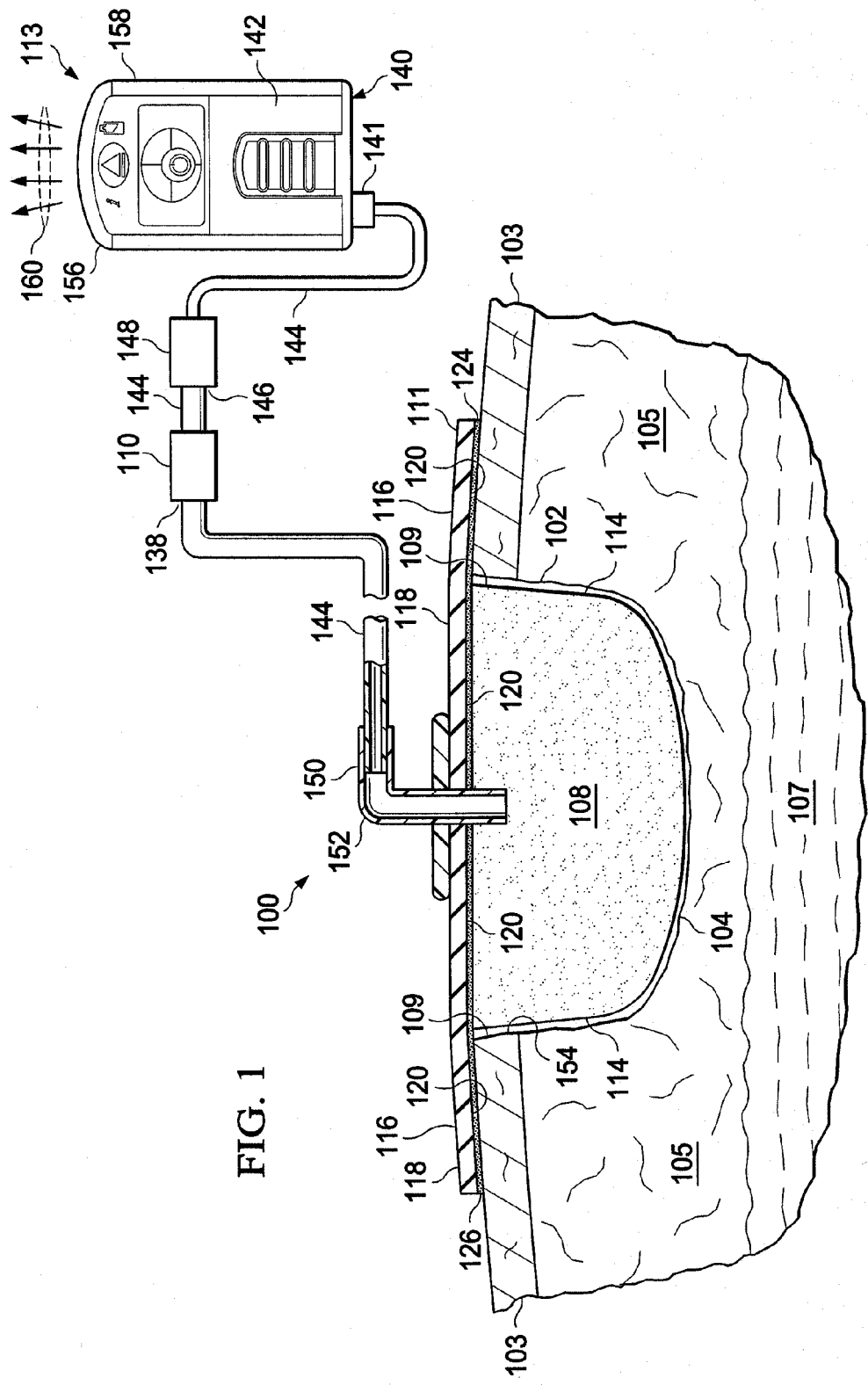
FIG. 1 is a schematic diagram with a portion shown in cross section of an illustrative embodiment of a reduced-pressure treatment system employing a reduced-pressure source.

Referring now to the drawings and primarily to FIG. 1, an illustrative embodiment of a reduced-pressure treatment system 100 for treating a tissue site 104, such as a wound 102, is presented. The wound 102 may be centered in a wound bed. The wound 102 may be through or involve epidermis 103, dermis 105, and subcutaneous tissue 107. The reduced-pressure treatment system 100 may also be used at other tissue sites. The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity.

The reduced-pressure treatment system 100 includes a treatment manifold 108. In addition, the reduced-pressure treatment system 100 includes a sealing member 111 and a reduced-pressure subsystem 113. The reduced-pressure subsystem 113 includes a reduced-pressure source 140 that is sealed to prevent liquid ingress and yet allows gas—typically air—to be vented without an aperture (i.e., a macroscopic aperture) as will be described further below.

In one illustrative embodiment, the treatment manifold 108 is made from a porous and permeable foam or foam-like material and, more particularly, a reticulated, open-cell polyurethane or polyether foam that allows good permeability of wound fluids while under a reduced pressure. One such foam material that has been used is the VAC® GranuFoam® Dressing available from Kinetic Concepts, Inc. (KCI) of San Antonio, Tex. Any material or combination of materials may be used for the manifold material provided that the manifold material is adapted to distribute the reduced pressure. The term "manifold" as used herein generally refers to a substance or structure that is provided to assist in applying reduced pressure to, delivering fluids to, or removing fluids from a tissue site. A manifold typically includes a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

The sealing member 111 covers the treatment manifold 108 and extends past a peripheral edge 114 of the treatment manifold 108 to form a sealing-member extension 116. The sealing-member extension 116 has a first side 118 and a second, patient-facing side 120. The sealing-member extension 116 may be sealed against epidermis 103 or against a gasket or drape by sealing apparatus 124, such as a pressure-sensitive adhesive 126. The sealing apparatus 124 may take numerous forms, such as an adhesive sealing tape, or drape tape or strip; double-side drape tape; pressure-sensitive adhesive 126; paste; hydrocolloid; hydrogel; or other sealing means. If a tape is used, the tape may be formed of the same material as the sealing member 111 with a pre-applied, pressure-sensitive adhesive. The pressure-sensitive adhesive 126 may be applied on the second, patient-facing side 120 of the sealing-member extension 116. The pressure-sensitive adhesive 126 provides a substantial fluid seal between the sealing member 111 and the epidermis 103, which, as used herein, is also deemed to include a gasket or drape against the epidermis 103. Before the sealing member 111 is secured to the epidermis 103, removable strips covering the pressure-sensitive adhesive 126 may be removed. As used herein, "fluid seal" means a seal adequate to maintain reduced pressure at a desired site given the particular reduced-pressure source or subsystem involved.

The sealing member 111 may be an elastomeric material or any material or substance that provides a fluid seal. "Elastomeric" means having the properties of an elastomer and generally refers to a polymeric material that has rubber-like properties. More specifically, most elastomers have an ultimate elongation greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, sealing member materials may include a silicone drape, 3M Tegaderm® drape, acrylic drape such as one available from Avery Dennison.

The reduced-pressure subsystem 113 includes the reduced-pressure source 140, which may take many different forms. The reduced-pressure source 140 provides reduced pressure as a part of the reduced-pressure treatment system 100. As used herein, "reduced pressure" generally refers to a pressure less than the ambient pressure at a tissue site 104 that is being subjected to treatment. In most cases, this reduced pressure will be less than the atmospheric pressure at which the patient is located. Alternatively, the reduced pressure may be less than a hydrostatic pressure at a tissue site. Reduced pressure may initially generate fluid flow in the treatment manifold 108, a reduced-pressure delivery conduit 144, and adjacent to the tissue site 104. As the hydrostatic pressure around the tissue site 104 approaches the desired reduced pressure, the flow may subside, and the reduced pressure may be maintained. Unless otherwise indicated, values of pressure stated herein are gauge pressures.

The reduced pressure delivered may be constant or varied (patterned or random) and may be delivered continuously or intermittently. Consistent with the use herein, an increase in reduced pressure or vacuum pressure typically refers to a reduction in absolute pressure.

The reduced-pressure source 140 is shown having a reservoir region 142, or canister region. An interposed membrane filter, such as hydrophobic or oleophobic filter, may be interspersed between the reduced-pressure delivery conduit 144, or tubing, and the reduced-pressure source 140. A portion 146 of the reduced-pressure delivery conduit 144 may have one or more devices, such as a representative device 148. The representative device 148 may be, for example, a fluid reservoir to hold exudates and other fluids removed, a pressure-feedback device, a volume detection system, a blood detection system, an infection detection system, a flow monitoring system, or a temperature monitoring system. Multiple representative devices 148 may be included in series or parallel. For example, a second representative device 110 may be included on a portion 138 of the reduced-pressure delivery conduit 144. Some of these devices may be formed integrally with the reduced-pressure source 140. For example, a reduced-pressure port 141 on reduced-pressure source 140 may include a filter member that includes one or more filters, e.g., an odor filter.

The reduced-pressure source 140 may be any device for supplying a reduced pressure, such as a portable therapy unit, a stationary therapy unit, or other device. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

The reduced pressure developed by reduced-pressure source 140 is delivered through the reduced-pressure delivery conduit 144 to a reduced-pressure interface 150, which may include an elbow port 152. In one illustrative embodiment, the elbow port 152 is a TRAC® technology port available from Kinetic Concepts, Inc. of San Antonio, Tex. The reduced-pressure interface 150 allows the reduced pressure to be delivered through the sealing member 111 to the treatment manifold 108, as well as to a sealed space 154, or sealed treatment space, in which the treatment manifold 108 is located. In this illustrative embodiment, the reduced-pressure interface 150 extends through the sealing member 111 and into the treatment manifold 108.

In operation according to one illustrative embodiment, the treatment manifold 108 is placed adjacent the tissue site 104, e.g., in the wound bed on wound 102, with a portion near a wound edge 109. The sealing member 111 is placed over the tissue site 104 and the treatment manifold 108 and at least partially against epidermis 103 (or gasket or drape) to form a fluid seal and the sealed space 154. If not already installed, the reduced-pressure interface 150 is installed. The reduced-pressure delivery conduit 144 is fluidly coupled to the reduced-pressure interface 150 and the reduced-pressure source 140 whereby reduced pressure may be provided to the treatment manifold 108. The reduced-pressure source 140 may be activated to begin the delivery of reduced pressure to the treatment manifold 108 in the sealed space 154.

Figure 2:
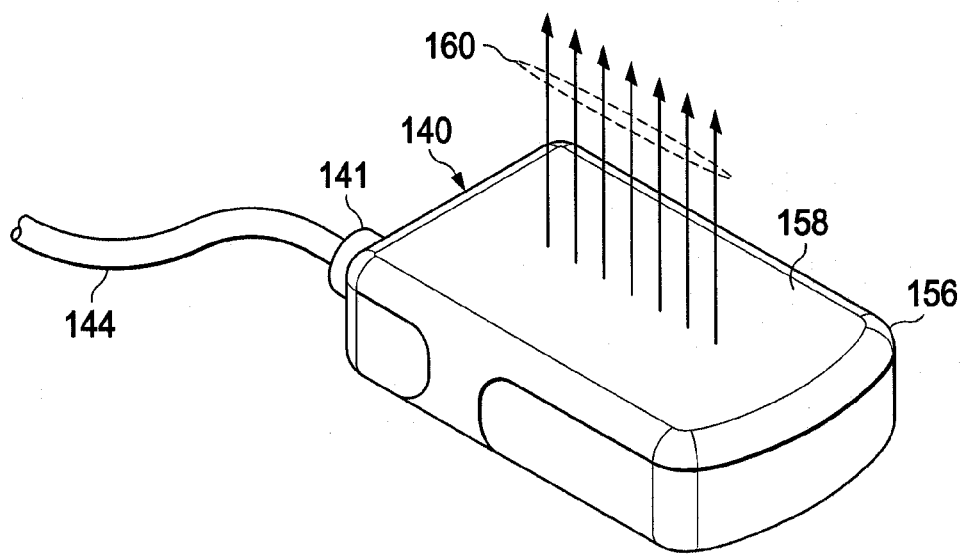
FIG. 2 is a schematic, perspective view showing a back side of an illustrative embodiment of the reduced-pressure source of FIG. 1.

Referring now primarily to FIGS. 1 and 2, the reduced-pressure source 140 is water proof or water resistant and uses a sealed space (not explicitly shown). The sealed space may be formed by two chambers or areas: one for positive pressure and one for reduced pressure. The reduced pressure chamber may be one or more conduits in the first chamber (e.g., conduits 268, 244 in FIG. 3). The sealed space is formed within a pump housing 156. The pump housing 156 is formed by or includes an enclosure member 158. The enclosure member 158 is formed from a polymeric, porous, hydrophobic material. The pump housing 156 may be formed completely using the enclosure member 158 or the enclosure member 158 may form only a portion of the pump housing 156.

A vacuum pump (not shown) is disposed within the sealed space. The polymeric, porous, hydrophobic material allows an exhaust gas from the vacuum pump within the sealed space to exit when under pressure while not allowing the ingress of fluids. The polymeric, porous, hydrophobic material allows the exhaust gas to exit without requiring a vent aperture, but instead uses pores and the properties of the material. The exhaust gas exiting the enclosure member 158 is represented by arrows 160. The sealed space also functions to make the reduced-pressure source 140 operate with a lower decibel level from a perspective of outside the pump housing 156. The vacuum pump may have a conduit associated with the vacuum pump that delivers reduced pressure from the vacuum pump through the sealed space to a reduced-pressure outlet (not shown) that is fluidly coupled to the reduced-pressure port 141.

The polymeric, porous, hydrophobic material may be any polymeric material that allows the exhaust gas to exit through the material and keeps fluids from entering the sealed space. The polymeric, porous, hydrophobic material is porous so in the first instance it will allow the passage of gas through its pores. The hydrophobic nature of the polymer, however, will block the passage of essentially aqueous liquids through the pores due to surface tension effects.

There is a relationship that describes the pressure required to push a liquid of a certain surface tension through an orifice, of a given pore size, of a material of a given surface energy (this pressure is sometimes called the "breakthrough pressure"). For example, to create a given breakthrough pressure for water passing through a pore could be achieved with a large pore low surface energy material, or a small pore high surface energy material. The following equation may be used to describe the relationship: $P = -2\sigma \cos \theta\, r$, where $P$=breakthrough pressure; $\theta$=contact angle between liquid and pore material (is a function of the surface energy of the contact surface and surface tension of the contacting liquid); $\sigma$=surface tension of the contacting liquid; and $r$=radius of the pore. In an embodiment, the breakthrough pressure is such that liquids do not break through for the pressure range involved. Thus, gas may exit, but liquids do not.

In on embodiment, the polymeric, porous, hydrophobic material is formed from a hydrophobic sintered polymer that is porous and gas permeable. Most polymers that can be made into a particulate may be used, e.g., polyolefins such as polyethylene, and polypropylene, polyamines, polyethylene vinyl acetate, polyvinyl chloride, styrenics (e.g., polystyrnene and copolymers including styrene acrylics), or polytetrafluoroethylene. The polymeric, porous, hydrophobic material may be a hydrophobic, spun-bonded high-density polyethylene fibers or material, such as a TYVEK® material form E.I. Du Pont De Nemours and Company Corporation of Wilmington, Del.

The polymeric, porous, hydrophobic material may also be formed with hydrophobic bonded, porous fibers. The polymeric, porous, hydrophobic material may also be formed by starting with a hydrophilic material and treating the material, e.g., with a plasma treatment, to make the material hydrophobic. Also, a hard polymer may be used that is caused to be porous by drilling micro-apertures (1 micron or sub micron), such as with a laser. If not already hydrophobic, the drilled polymer may be treated with a plasma. In addition, an odor-absorbing material may be added to the polymeric, porous, hydrophobic material to help remove odors as the exhaust gas exits. The odor-absorbing material may be, for example, charcoal, clays such as bentonite clay, porous silicas, zeolites, and aluminas, or substrates and supports that contains charcoal or activated carbon, for example polymeric meshes and membranes. Other substances may be added such as anti-microbials, silver, or dyes.

The pump housing 156 may be formed completely by injection, or transfer, or compression, or rotational molding, or thermoforming (vacuum forming) using the polymeric, porous, hydrophobic material. In another embodiment, the pump housing 156 may be formed with a first portion, or enclosure member 158, formed from the polymeric, porous, hydrophobic material and a second portion formed from a polymer or other material having greater rigidity than the polymeric, porous, hydrophobic material. As will be described further below, the pump housing 156 may also be a dressing covering in some embodiments. The pump housing 156 may be made to be flexible and translucent if desired. The translucent portion allows visual feedback on what is occurring in the sealed space. A liquid-sensitive dye may be associated with the pump housing 156 by either including it in the polymeric, porous, hydrophobic material or coating the polymeric, porous, hydrophobic material. The liquid-sensitive dye changes color upon becoming wet and thus serves as a leak indicator.

While FIGS. 1 and 2 show the polymeric, porous, hydrophobic material utilized as an enclosure member 158 on a pump housing 156, it should be understood that the enclosure member 158 may be used as the pump housing 156, a vent panel, or a dressing cover depending on the desired application. With the reduced-pressure source 140, which is portable in the illustrative embodiment shown in FIG. 1, the sealed space is substantially liquid-tight and, thus, the wearer may engage in activities subject to fluids on the exterior, e.g., taking a shower, without fluids entering the reduced-pressure source 140.

Figure 3:
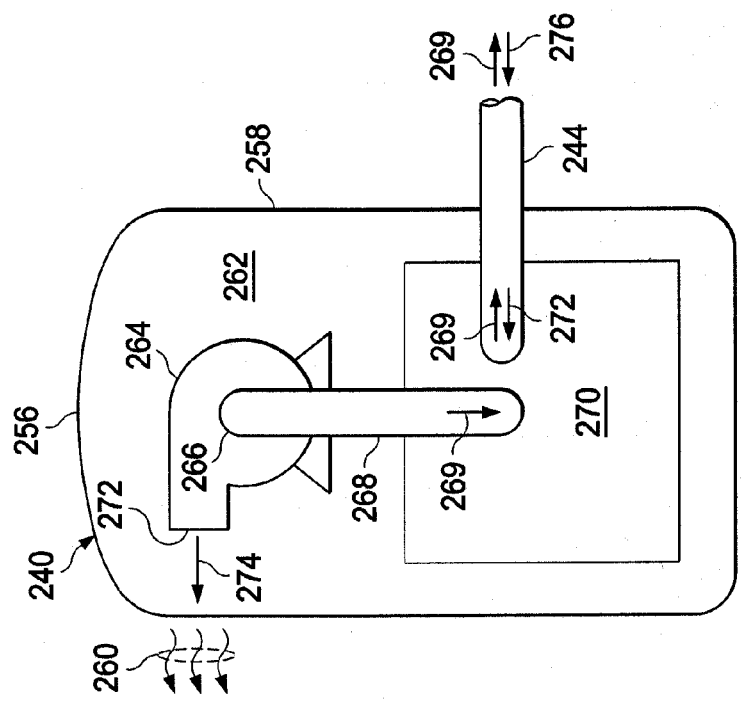
FIG. 3 is a schematic diagram of an illustrative embodiment of a reduced pressure source.

Referring now primarily to FIG. 3, a schematic diagram of a reduced-pressure source 240 is presented that has a portion removed to allow components in a sealed space 262 to be visible. The reduced-pressure source 240 has a pump housing 256. The pump housing 256 may be formed totally or in part by an enclosure member 258. The pump housing 256 forms the sealed space 262. Accordingly, the sealed space 262 may be formed in part or totally by the enclosure member 258. The sealed space 262 is sealed to prevent or inhibit the ingress of liquids, such as water, and also inhibits the entry of particulates, such as dust.

A vacuum pump 264, which may include any device for generating a reduced pressure, is disposed within the sealed space 262. The vacuum pump 264 has a reduced-pressure outlet 266 that is fluidly coupled to the vacuum pump 264 and that discharges reduced pressure 269 out of the vacuum pump 264. In this embodiment, the reduced-pressure outlet 266 is fluidly coupled to a transport conduit 268, which is a second chamber. The transport conduit 268 delivers the reduced pressure to a canister 270. The canister 270 is for receiving and retaining fluids, such as exudates. The canister 270 is fluidly coupled to a reduced-pressure delivery conduit 244. The vacuum pump 264 also has an exhaust outlet 272 that discharges exhaust 274, or exhaust gas 274, from the vacuum pump 264. The reduced-pressure delivery conduit 244 delivers reduced pressure 269 to another location, such as a tissue site, and typically receives fluids 276.

The exhaust 274 is delivered into the sealed space 262. As the exhaust gas 274 increases the pressure within the sealed space 262, the exhaust gas 274 is moved through the enclosure member 258 as suggested by arrows 260 without a vent aperture. The enclosure member 258 is made from the same materials and in the same various ways as the enclosure member 158 in FIGS. 1-2. Thus, the exhaust 274 exits through pores in the enclosure member 258.

Figure 4:
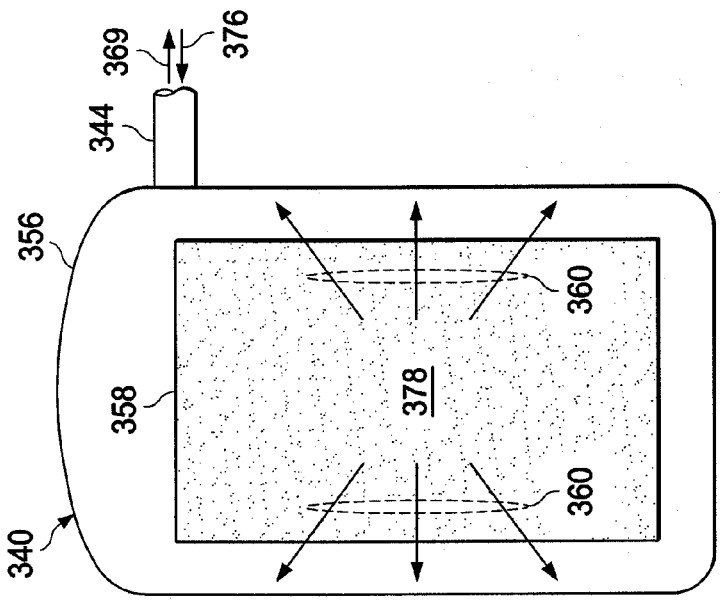
FIG. 4 is a schematic, front view of an illustrative embodiment of a reduced-pressure source.

Referring now primarily to FIG. 4, another illustrative embodiment of a reduced-pressure source 340 is presented. The reduced-pressure source 340 is analogous in most respects to the reduced-pressure source 240 of FIG. 3, and to show corresponding parts, the reference numerals have been indexed by 100. Thus, the reduced-pressure source 340 has a pump housing 356 that forms a sealed space (not explicitly shown) in which a vacuum pump (not shown) is disposed.

In this embodiment, a portion of the pump housing 356 is an enclosure member 358 that comprises a vent panel 378, which is gas permeable. The other portions of the pump housing 356 may not be gas permeable. The vent panel 378 is made of the same type of materials as and may be regarded as an enclosure member (e.g., enclosure member 158 of FIG. 1). The vent panel 378 is adapted to allow the exhaust gas 360 to exit the sealed space without allowing liquids to enter and without requiring a vent aperture. The size of the vent panel 378 is dependent on the desired gas flow rate across the vent panel 378. Reduced pressure 369 is delivered through a reduced-pressure delivery conduit 344. Fluids 376 may also be received by the reduced-pressure delivery conduit 344.

In forming the vent panel 378 and pump housing 356, a laminate member of the polymeric, porous, hydrophobic material is formed into the vent panel 378. The vent panel 378 may then be overmolded to form the pump housing 356. This creates the vent panel 378 for allowing exhaust gases to exit the sealed space. The size of the vent panel will be determined by the need for an adequate flow rate of the exhaust gas from the sealed space.

According to one illustrative embodiment, the pump housing 356 and vent panel 378 are formed by starting with a filter block, or a laminate of filter material, and then overmolding, i.e., molding around the filter block in an injection molding process. Alternatively, the filter block or laminate may be bonded in place using a liquid or pressure sensitive sheet adhesive or otherwise attached.

Figure 5:
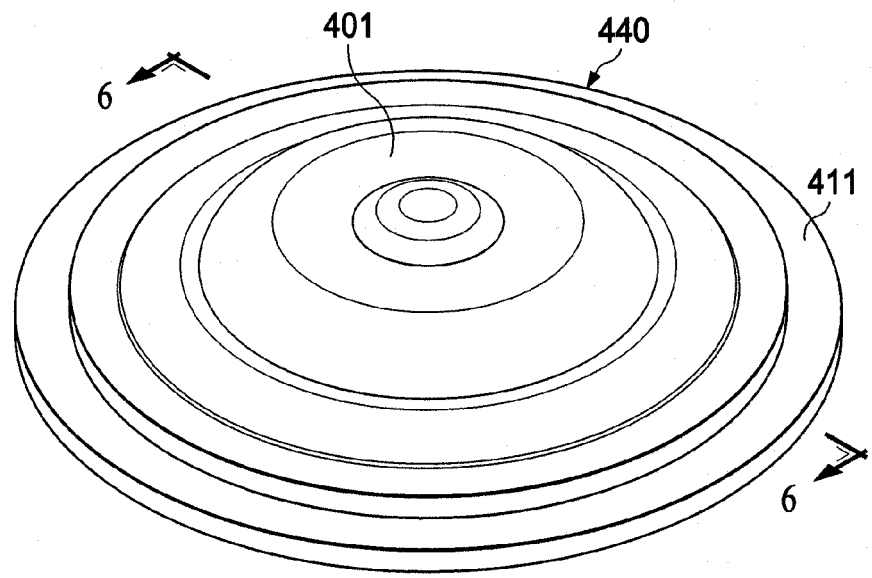
FIG. 5 is a schematic, perspective view of another illustrative embodiment of a reduced-pressure source shown as part of a dressing.
Figure 6:
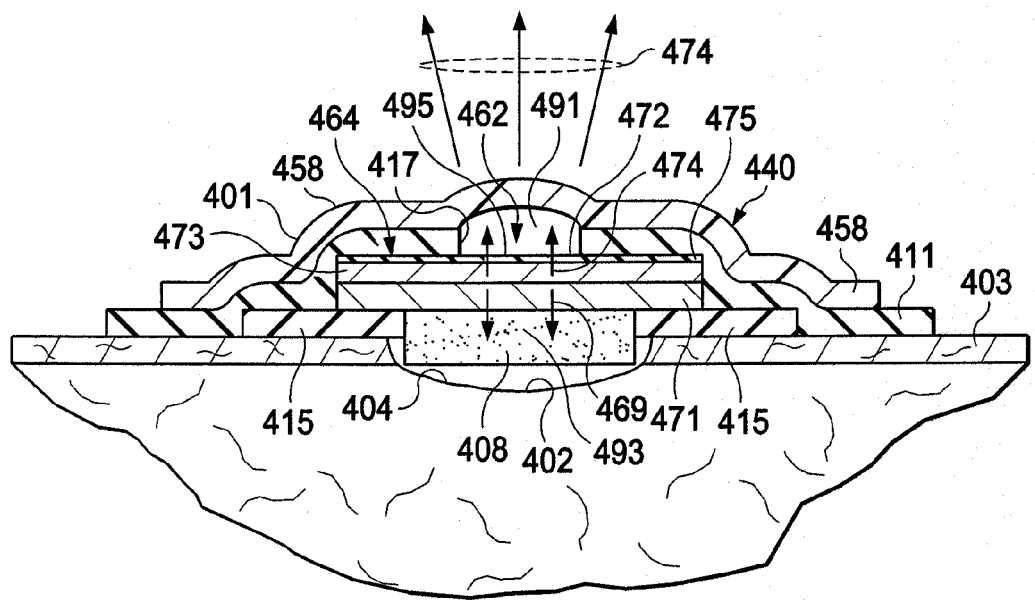
FIG. 6 is a schematic cross sectional view of a portion of the reduced-pressure source of FIG. 5.

Referring now primarily to FIGS. 5-6, another illustrative embodiment of a reduced-pressure source 440 is presented. The reduced-pressure source 440 is incorporated into a dressing 401 that is placed on a tissue site 404, such as a wound 402. The dressing 401 includes a treatment manifold 408 and a sealing layer 415. A micro-pump 464 is included to provide reduced pressure 469 to the treatment manifold 408 and to the tissue site 404.

The micro-pump 464 may include a piezoelectric disc pump, a diaphragm pump, a piston pump, a peristaltic pump, or other means of creating reduced pressure in a small space. The dressing 401 may also include a number of layers. For example, the dressing 401 may include an absorbent layer 471 that delivers or helps deliver reduced pressure and receives and retains fluids and may include a liquid-air separator 473 that is positioned between the absorbent layer 471 and the micro-pump 464 to inhibit liquid from entering the micro-pump 464. A diverter layer 475 may be disposed between the absorbent layer 471 and the micro-pump 464 that may include apertures (not shown) for transmitting reduced pressure from the micro-pump 464 to the absorbent layer 471. The micro-pump 464 may also include one or more batteries and controls (not shown).

The sealing member 411 may be deployed over a portion of the micro-pump 464, the sealing layer 415, and a portion of the patient's epidermis 403. The sealing member 411 may have a central aperture 417 over a portion of the micro-pump 464. An enclosing cover 458, which may be flexible or semi-flexible as with other members, is disposed over the central aperture 417 and a portion of the sealing member 411 to created a sealed space 462. The sealed space 462 may have two portions: a first portion 491 above (for the orientation shown) the micro-pump 464 and a second portion 493 below (for the orientation shown) the micro-pump 464. The first portion 491 is fluidly coupled to the micro-pump 464 and receives exhaust from an exhaust outlet 495 of the micro-pump 464. The second portion 493 is also fluidly coupled to the micro-pump 464 and receives reduced pressure from the micro-pump 464. At least a portion of the enclosing cover 458 is formed from a polymeric, porous, hydrophobic material that allows the exhaust to egress the first portion of the sealed space 462. That is, the enclosing cover 458, or at least a portion of the enclosing cover 458, is formed from the same materials as the previously-mentioned enclosure members 158, 258, 358, i.e., a polymeric, porous, hydrophobic material.

The central aperture 417 allows exhaust 474 from an exhaust outlet 472, which is on the surface of the micro-pump 464 in this embodiment, to exit the sealing member 411 and impinge upon the enclosing cover 458. As pressure rises, the exhaust gas 474 exits through the polymeric, porous, hydrophobic material of the enclosure member 458. Fluids removed by the micro-pump 464 may be stored in the absorbent layer 471 of the dressing 401. In another embodiment, the enclosure member 458 may only comprise a portion of a cover over the absorbent layer 471 and the micro-pump 464, and in this embodiment, the enclosure member 458 covers at least the central aperture 417. In an alternative embodiment, the sealing member 411 may comprise the enclosure member 458.

Although the present invention and its advantages have been disclosed in the context of certain illustrative embodiments, it should be understood that various changes, substitutions, permutations, and alterations can be made without departing from the scope of the invention as defined by the appended claims.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A reduced-pressure source for treating a tissue site, the reduced-pressure source comprising:
    a pump housing comprising walls forming a sealed space;
    a vacuum pump disposed within the walls of the pump housing;
    a reduced-pressure outlet fluidly coupled to the vacuum pump, and configured to provide reduced pressure generated by the vacuum pump to a reduced-pressure chamber disposed within the walls of the pump housing; and
    an exhaust outlet: (i) disposed within and fluidly coupled to the sealed space; (ii) fluidly coupled to the vacuum pump; and (iii) configured to discharge a positive pressure exhaust gas generated by the vacuum pump into a positive-pressure chamber in the sealed space;
    wherein a hydrophobic polymer forms a substantial portion of at least one wall of the walls of the pump housing and is configured so that the positive pressure exhaust gas exits the sealed space through the hydrophobic polymer and wherein the hydrophobic polymer is further configured to prevent liquid ingress into the sealed space from an exterior of the pump housing.

2. The reduced-pressure source of claim 1, wherein the hydrophobic polymer comprises a sintered polymer.

3. The reduced-pressure source of claim 1, wherein the hydrophobic polymer comprises spun-bonded fibers.

4. The reduced-pressure source of claim 1, wherein the hydrophobic polymer is formed from hydrophobic fibers.

5. The reduced-pressure source of claim 1, wherein the reduced-pressure chamber comprises a conduit fluidly coupled to the reduced-pressure outlet.

6. The reduced-pressure source of claim 1, wherein the reduced-pressure chamber further comprises a conduit configured to deliver reduced pressure from the vacuum pump to a canister for receiving fluid from the tissue site.

7. The reduced-pressure source of claim 1, wherein the hydrophobic polymer forms a panel of at least one wall of the pump housing.

8. A reduced-pressure source for treating a tissue site, the reduced-pressure source comprising:
    an enclosure member having walls forming a sealed space and comprising therein a positive-pressure chamber, a reduced-pressure chamber, and a vacuum pump;
    a reduced-pressure outlet fluidly coupled to the vacuum pump and configured to provide reduced pressure from the vacuum pump to the reduced-pressure chamber; and
    an exhaust outlet: (i) disposed within the walls of the enclosure member; (ii) fluidly coupled to the sealed space and to the vacuum pump; and (iii) configured to discharge a positive pressure exhaust gas from the vacuum pump to the positive-pressure chamber;

wherein the enclosure member comprises a hydrophobic polymer forming a substantial portion of at least one wall of the walls and configured so that the positive pressure exhaust gas from the positive-pressure chamber exits the enclosure member through the hydrophobic polymer.

9. The reduced-pressure source of claim 8, wherein the reduced-pressure chamber further comprises a conduit fluidly coupled to the reduced-pressure outlet.

10. The reduced-pressure source of claim 8, wherein the hydrophobic polymer of the at least one wall of the walls of the enclosure member is configured to inhibit ingress of liquid into the sealed space from an exterior of the enclosure member.

11. The reduced-pressure source of claim 8, wherein the hydrophobic polymer comprises a sintered polymer.

12. The reduced-pressure source of claim 8, wherein the hydrophobic polymer comprises spun-bonded fibers.

13. The reduced-pressure source of claim 8, wherein the hydrophobic polymer is formed from hydrophobic fibers.

14. The reduced-pressure source of claim 8, further comprising a canister fluidly coupled to the reduced-pressure chamber.

15. The reduced-pressure source of claim 8, wherein the hydrophobic polymer comprises micro-apertures of 1 micron or less.

16. An apparatus for providing reduced pressure to a tissue site, the apparatus comprising:
a vacuum pump disposed within an enclosure member having walls forming a sealed space, the walls of the enclosure member further enclosing therein a reduced-pressure chamber and a positive-pressure chamber;
a reduced-pressure outlet fluidly coupled to the vacuum pump and configured to provide reduced-pressure generated by the vacuum pump to the reduced-pressure chamber; and
an exhaust outlet: (i) disposed within the walls of the enclosure member; (ii) fluidly coupled to the sealed space and to the vacuum pump; and (iii) configured to discharge a positive pressure exhaust gas generated by the vacuum pump to the positive-pressure chamber;
the enclosure member comprising a hydrophobic polymer forming a substantial portion of at least one wall of the walls, the hydrophobic polymer configured to inhibit ingress of liquid to the vacuum pump from an exterior of the enclosure member and to allow the positive pressure exhaust gas to exit the enclosure member through the hydrophobic polymer.

17. The apparatus of claim 16, further comprising a canister fluidly coupled to the reduced-pressure chamber.

18. The apparatus of claim 16, further comprising:
a treatment manifold configured to distribute reduced pressure across the tissue site; and
a sealing member configured to cover the treatment manifold.

19. The apparatus of claim 16, wherein the hydrophobic polymer is a sintered polymer.

20. The apparatus of claim 19, further comprising:
a canister fluidly coupled to the reduced-pressure chamber;
a treatment manifold fluidly coupled to the canister; and
a sealing member configured to cover the treatment manifold.

* * * * *